United States Patent [19]
Phillips

[11] Patent Number: 6,113,573
[45] Date of Patent: Sep. 5, 2000

[54] FOLEY CATHETER CUSTOMIZATION

[76] Inventor: Jean Pierre Phillips, 4036 NE. 73$^{rd}$ Ave., Portland, Oreg. 97213

[21] Appl. No.: 09/118,139

[22] Filed: Jul. 16, 1998

[51] Int. Cl.$^7$ ................................................ A61M 29/00
[52] U.S. Cl. ......................... 604/96; 604/523; 604/534; 604/535
[58] Field of Search ............................ 604/96, 500, 523, 604/905, 534, 535, 539

[56] References Cited

U.S. PATENT DOCUMENTS 5,645,528  7/1997  Thome ...................................... 604/96

*Primary Examiner*—John D. Yasko
*Attorney, Agent, or Firm*—Marger Johnson & McCollom, P.C.

[57] ABSTRACT

A catheter fitting and method for its use are described. The fitting allows the length of a catheter to be customized, since it joins two catheter ends. The length of either or both ends can be adjusted to achieve a desired overall catheter length.

3 Claims, 3 Drawing Sheets

FOLEY CATHETER CUSTOMIZATION

BACKGROUND OF THE INVENTION

Normal catheters sold on the market today are too long, which can cause a number of problems physically and emotionally to both patient and their physicians who try to meet their needs. The extra tubing hanging loose can become entangled easily and has a tendency to bunch up a great deal, causing stress, anxiety, frustration and embarrassment to a patient who must wear a catheter.

SUMMARY OF THE INVENTION

In the present invention we have designed a new fitting that can change any normal catheter or drainage tube to make it shorter or longer to fit anyone's need. With our new fittings a patient can now have more choices and freedom to wear the clothing that fits their lifestyle, even wear a two-piece swim suit with little or no detection of the super pubic tube.

Sex and intimacy is a major problem because of embarrassment due to the very long catheter hanging loose in the are in which sex and intimacy take place. With a five inch super pubic tube catheter in place a patient cover the entire tube with a large, flesh colored band-aid which hides the tube, easing the embarassment and making life more normal and enjoyable under the circumstances.

There is a great need for this new product in the market today. It will be very useful in all areas of the medical field because of its ability to shorten or lengthen any catheter or drainage tube. It allows both consumer and physician more choices to meet everyone's need and/or lifestyle.

The invention may be best understood by reading the disclosure with reference to the drawing, wherein.

DETAILED DESCRIPTION OF THE INVENTION

Figure 2A:
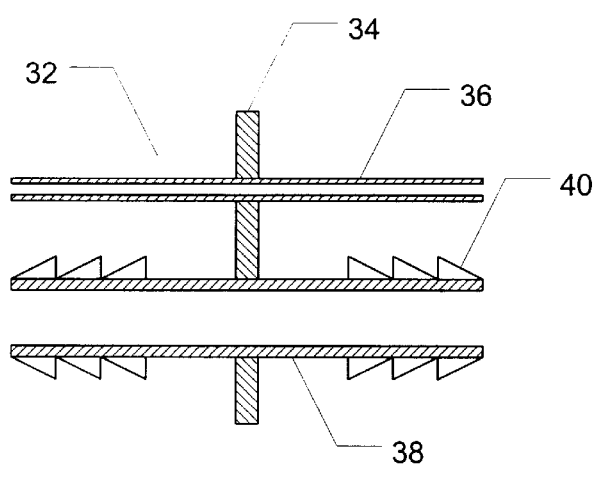
FIGS. 2A and 2B illustrate, respectively, a section view and an end view of a catheter fitting according to an embodiment of the invention.
Figure 2B:
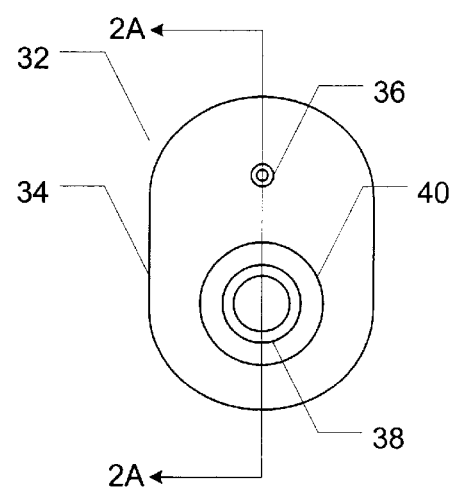

FIG. 2A and 2B illustrate a catheter fitting 23 according to one embodiment of the invention. A fitting shoulder or bracket 34 is secured to a pressure tube 36 and a fluid tube 38. Shoulder 34 holds tubes 36 and 38 in a spaced-apart arrangement as required for a particular catheter application. The configuration of each tube (length on each side of fitting, number or presence/absence of nipple ribs 40, etc.) may be varied.

The fittings are preferably manufactured wiht strength and integrity in mind and will not bend, break or collapse under any condition wiht normal use. Preferred materials are those that are FDA approved for medical use. The dimensions of each fitting vary depending on the diameter size of the catheter used. The pressure and flow rate is the same as any normal catheter sold on the market today, The only thing we have changed is the ability to make them shorter or longer to custom fit anybody's shape or size enabling them to live a more carefree and normal life without the embarassment and frustration of the normal, longer catheters sold today.

Figure 1:
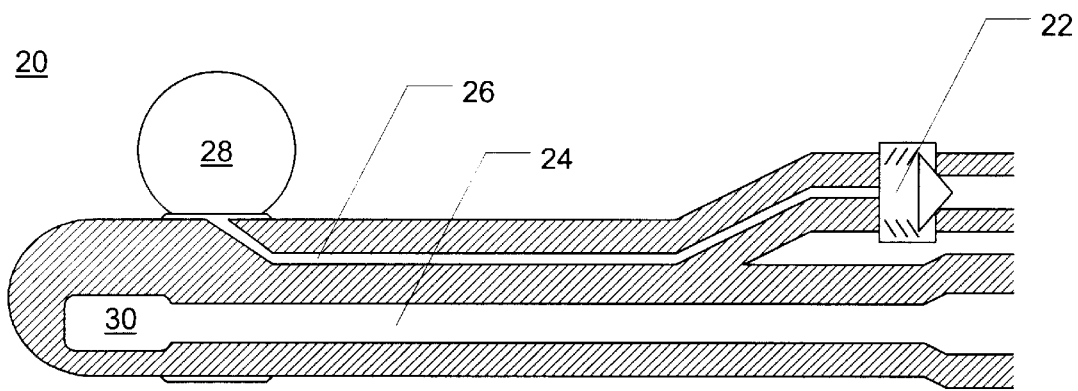
FIG. 1 illustrates a cross-section of a prior art catheter.
Figure 3:
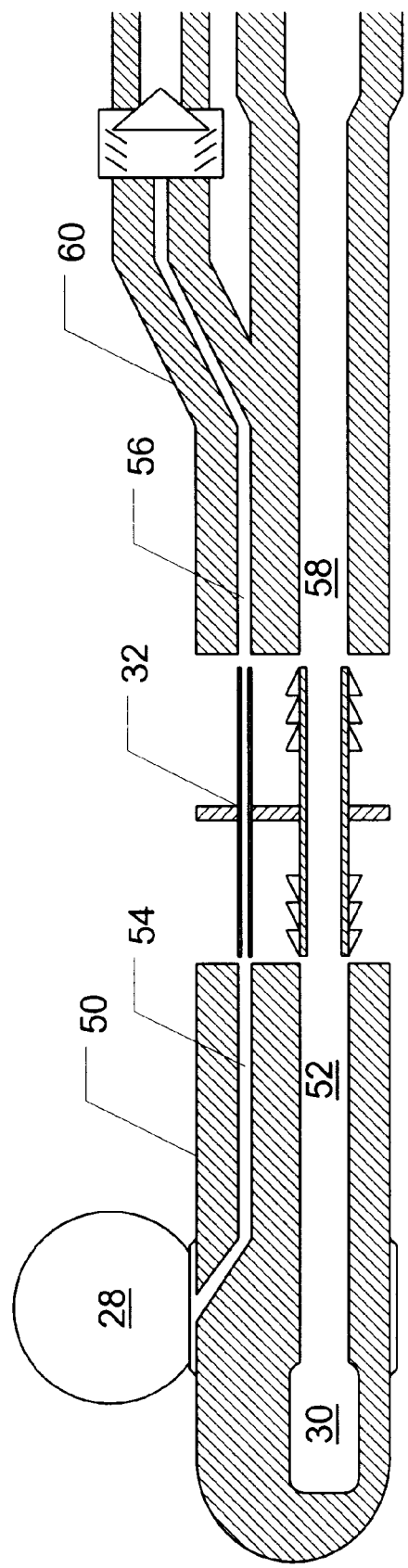
FIG. 3 illustrates a cross-section of a catheter end, a catheter fitting, and a catheter main tube in an exploded arrangement.
Figure 4:
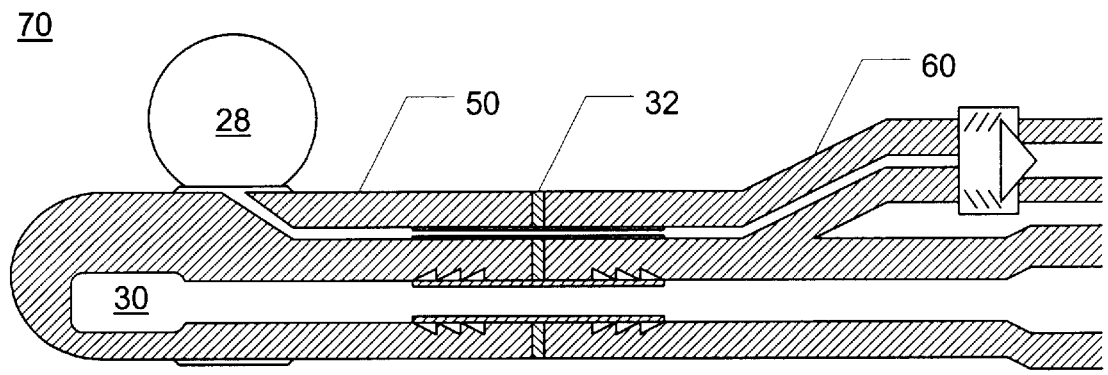
FIG. 4 illustrates a cross-section of a catheter end, a catheter fitting, and a catheter main tube in an assembled view.

In the preferred method of use, fitting 32 is used to join a catheter end 50 and a catheter main tube 60, as shown in FIGS. 3 and 4. Fitting 32 joins pressure tube 54 of catheter end 50 with pressure tube 56 of catheter main tube 60, and also joins fluid flow tube 52 of catheter with fluid flow tube 58 of catheter main tube 60. Catheter end 50 and main tube 60 can be created by cutting a standard catheter such as catheter 20 of FIG. 1. To make a shorter catheter, either catheter end 50 or main tube 60 can be shortened. To make a longer catheter, a longer catheter end 50 or main tube 60 can be selected for mating using fitting 32.

The fittings are manufactured with strength and integrity in mind and will not bend, break or collapse under any condition with normal use. The fittings are custom made from our own drafting by a local company in Portland, Oreg. The new fittings are FDA approved for medical use and are patent pending at this time. The dimensions of each fitting vary depending on the diameter size of the catheter used. The pressure and flow rate is the same as any normal catheter sold on the market today. The only thing we have changed is the ability to make them shorter or longer to custom fit anybody's shape or size enabling them to live a more carefree and normal life without the embarrassment and frustration of the normal, longer catheters sold today.

What is claimed is:

1. A catheter apparatus comprising:

a bracket;

a pressure tube nipple mounted on the bracket and having first and second ends;

a fluid flow nipple mounted on the bracket, and having first and second ends;

a first catheter tube portion having a first pressure tube and first fluid tube, the first pressure tube connected to the pressure tube nipple first end, and the first fluid flow tube connected to the fluid flow tube nipple first end; and a second catheter tube portion having a second pressure tube and a second fluid tube, the second pressure tube connected to the pressure tube nipple second end, and the second fluid flow tube connected to the fluid flow tube nipple second end.

2. A catheter fitting comprising:

a bracket;

a first tube mounted to the bracket and having first and second ends protruding from the bracket;

a second tube mounted to the bracket and having first and second ends protruding from the bracket, the second tube substantially parallel to the first tube.

3. The catheter fitting of claim 2, wherein the first tube is a fluid flow tube having an outside diameter allowing it to fit snugly within a catheter fluid tube, and the second tube is a pressure tube having an outside diameter allowing it to fit snugly within a catheter pressure tube.

* * * * *